US00PP20749P3

(12) United States Plant Patent
Preil

(10) Patent No.: US PP20,749 P3
(45) Date of Patent: Feb. 16, 2010

(54) ***RHODODENDRON* ROOTSTOCK NAMED 'RHODUNTER 149'**

(50) Latin Name: ***Rhododendron* hybrid**
Varietal Denomination: Rhodunter 149

(75) Inventor: Walter Preil, Ammersbek (DE)

(73) Assignee: Inkarho GmbH, Bad Zwischenahn (DE)

( * ) Notice: Subject to any disclaimer, the term of this patent is extended or adjusted under 35 U.S.C. 154(b) by 59 days.

(21) Appl. No.: 12/070,196

(22) Filed: Feb. 15, 2008

(65) Prior Publication Data

US 2008/0235834 P1 Sep. 25, 2008

(51) Int. Cl.
*A01H 5/00* (2006.01)

(52) U.S. Cl. ..... Plt./238
(58) Field of Classification Search ..... Plt./238
See application file for complete search history.

(56) References Cited

OTHER PUBLICATIONS

"The International Rhododendron Register and Checklist (2004)-Third Supplement".*

* cited by examiner

*Primary Examiner*—Susan B McCormick Ewoldt
(74) *Attorney, Agent, or Firm*—The Webb Law Firm

(57) ABSTRACT

A new and distinct *Rhododendron* hybrid plant used as a rootstock that exhibits a high lime tolerance and vigorous growth.

2 Drawing Sheets

Botanical classification: *Rhododendron* hybrid.
Varietal denomination: 'Rhodunter 149'.

BACKGROUND OF THE INVENTION

The present invention comprises a new and distinct cultivar of *Rhododendron* hybrid used as a rootstock known by the varietal name 'Rhodunter 149'. The new variety was discovered in Ahrensburg, Germany. The new variety is the result of a planned breeding program between an unpatented *Rhododendron fortunei* (female parent) and C.V. 'Cunningham's White' (unpatented male parent). 'Rhodunter 149' exhibits leaves and flowers that are more similar to its female parent than to its male parent. Additionally, 'Rhodunter 149' exhibits more vigorous growth when compared to its male parent. Further, the new variety differs from both parents in its improved tolerance to lime. In fact, such improved lime tolerance (no Fe-deficiency symptoms on soils up to 6.9 pH) distinguishes the new variety from other *Rhododendron* varieties known to the breeder. The flower color of the new variety starts out as a strong lilac at bud stage and opens into a light lilac color. Its female parent has mostly white and bright pink flowers, and its male parent has white flowers. The new variety and its female parent bloom with fragrant flowers one to two weeks later than its male parent. Finally, 'Rhodunter 149' is a compact, bushy shrub. 'Rhodunter 149' has been trial and field tested and has been found to retain its distinctive characteristics and remain true to type through successive propagations.

DESCRIPTION OF THE DRAWINGS

The accompanying photographic drawings illustrate a four year old plant of the new variety, with the color being as nearly true as is possible with color illustrations of this type.

DESCRIPTION OF THE PLANT

Figure 1:
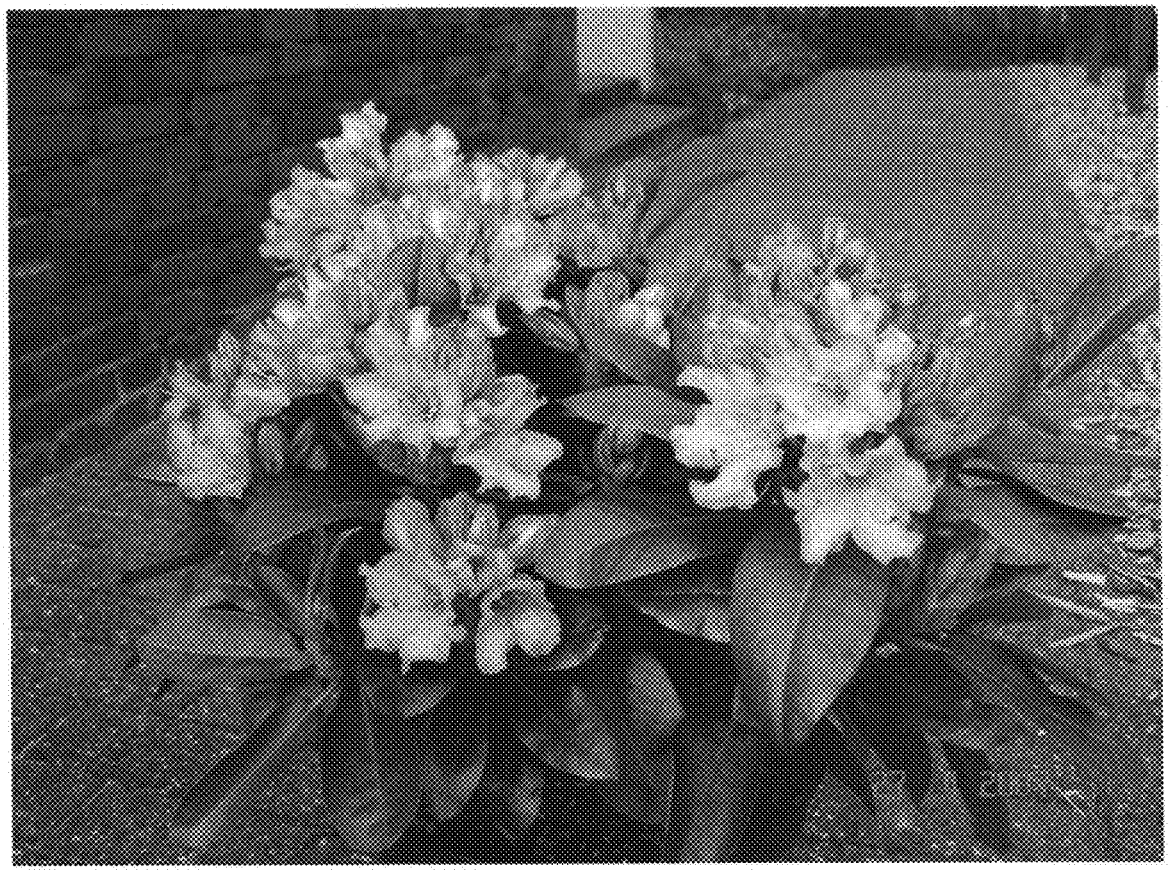
FIG. 1 shows a view of a typical flowering plant of the new variety grown to a flowering plant.
Figure 2:
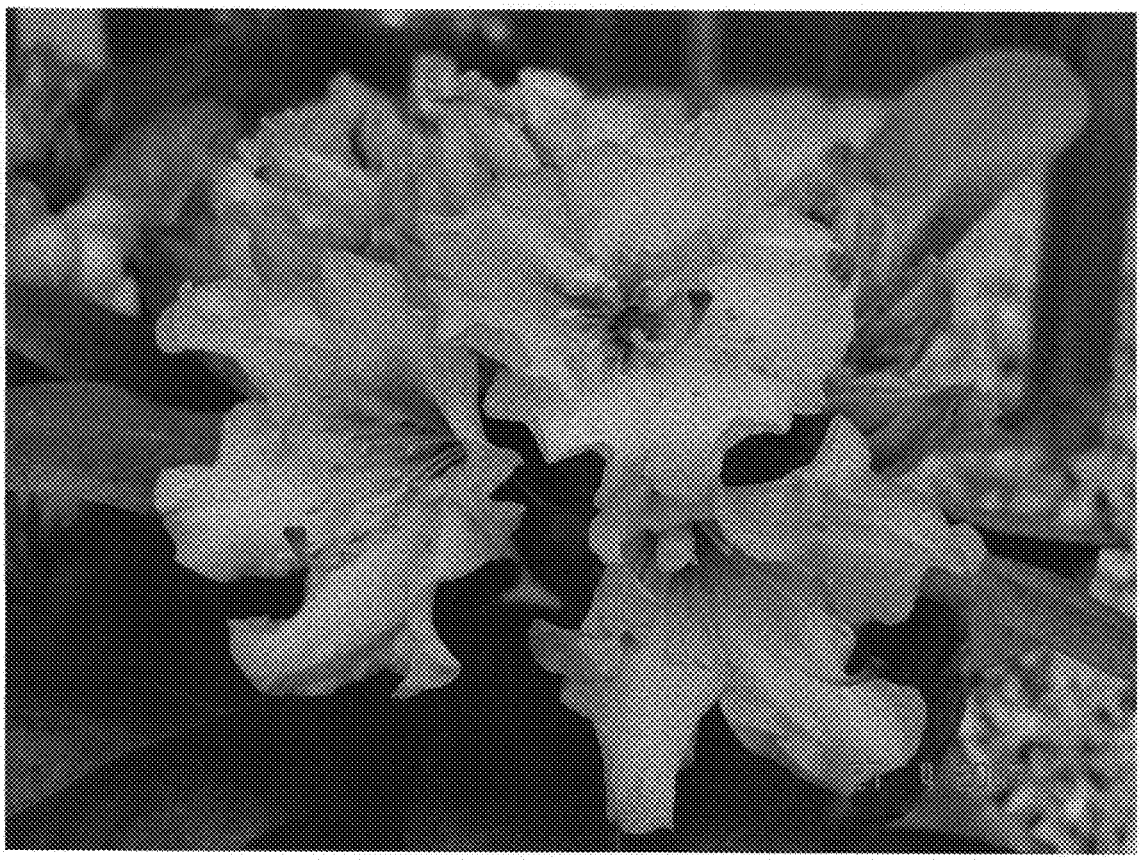
FIG. 2 shows a close-up view of the inflorescences of the new variety.

The following detailed description sets forth the characteristics of the new cultivar. The data which defines these characteristics were collected by asexual reproductions performed via cuttings or in vitro culture carried out in Ahrensburg, Germany. The color readings were taken in natural daylight. The new variety was four years old when described, except where expressly stated otherwise. Color measurements were taken outside under natural daylight. Color references are primarily to The R.H.S. Colour Chart of The Royal Horticultural Society of London.

PLANT

Time to initiate roots: About 90 days at 22–25° C.
Time to produce a finished flowering plant from a rooted cutting: About 4 years in the field.
Rooting habit: Compact root bales.
Form: Spreading.
Height: 50 cm at 3 years.
Diameter: 40 cm at 3 years.
Vigor: Strong.
Branching habit: Compact.
Disease, drought and pest resistance: No observations made to date.
Trunk (at 4 years):
- *Diameter.*—3 cm.
- *Height.*—5 cm above soil.
- *Bark color.*—Year one: 144A. Year two: From 144A to 175A. Year three: 175A. Year four and older: 177B to between 197B and 197C.
- *Texture.*—Smooth with fissured bark.
- *Pubescence.*—Absent.
- *Form.*—Erect.

Lateral Branches:

*Diameter.*—5–7 mm.

*Internode length.*—1–2 cm.

*Texture.*—Smooth with fissured bark.

*Pubescence.*—Absent.

*Color.*—Year one: 144A. Year two: From 144A to 175A. Year three: 175A. Year four and older: 177B to between 197 B and 197C.

Leaves:

*Arrangement.*—Alternate.

*Length.*—20 cm maximum.

*Width.*—7.5 cm maximum.

*Shape.*—Oblanceolate.

*Apex.*—Broad.

*Base.*—Tapering.

*Pubescence.*—Absent.

*Color.*—Upper surface: 147B for young leaves and 147A for mature leaves. Lower surface: 147C for both young and mature leaves.

*Margins.*—Entire.

*Venation pattern.*—Dense venation with a pronounced central vein.

*Vein color.*—Upper surface: 144A. Lower surface: 145C.

*Stipules.*—None present.

*Bracts.*—None present.

*Petiole.*—Shape: Round with a flat upside. Length: 2 cm. Diameter: 3–4 mm. Upper surface color: 144A. Lower surface color: 144C.

*Pedicel.*—Length: 4 cm. Width: 2 mm. Color: 144C.

Flower:

*Natural flowering season.*—Beginning of May until the end of May in Northern Germany.

*Form.*—Widely funnel-shaped.

*Arrangement.*—Truss.

*Lastingness of bloom.*—Approximately three weeks; from the beginning of May until the end of May.

*Average number of blooms.*—One bloom period per year.

*Fragrance.*—Typical of *Rhododendron fortunei.*

*Buds* (*described before bursting*).—Shape: Oblong. Width: 20 mm. Length: 40 mm. Color: 67A.

*Spike.*—Number of flowers per spike: 10–15. Length: 15 cm. Diameter: 15 cm.

*Corolla petals.*—Shape: Widely funnel-shaped. Number: 7. Length: 45–55 mm. Width: 80 mm. Apex: Round. Margin: Undulate. Color: When opening: 67B. Fully opened (upper surface): 74C to 74D. (lower surface): The external part is 84B, and the inner part is 84C.

*Corolla throat.*—Tube length: 20 mm. Color: 153A. Texture: Velvety smooth.

*Sepals.*—None present (totally reduced).

*Petaloids.*—None present.

Reproductive organs:

*Stamens.*—Number: 14. Length: 30 mm.

*Anthers.*—Shape: Normal *Rhododendron* type. Color: 161D. Length: 25 mm.

*Pollen.*—Amount of pollen: Typical for a *Rhododendron* plant. Color of pollen: 150D.

*Pistil.*—Number: 1. Style: Color: 160D. Length: 45 mm; filiform. Stigma: Shape: Undivided. Color: 145A.

Seeds:

*Production.*—Seed capsules mature in November when pollinated in May.

*Length.*—2 mm.

*Color.*—164B.

*Number.*—Approximately 200 per capsule.

COMPARISON WITH OTHER *RHODODENDRON* CULTIVARS

'Rhodunter 149' differs from 'Nova Zembla' (not patented) in that 'Rhodunter 149' is lime tolerant while 'Nova Zembla' is not. 'Rhodunter 149' has an upright growth habit while 'Nova Zembla' has a broad sweeping growth habit. 'Rhodunter 149' is very stable and has strong shoots while 'Nova Zembla' has thinner and less strong shoots. 'Rhodunter 149' has elongated and oval leaves while 'Nova Zembla' has vaulted and concave leaves with a slightly twisted leaf apex.

I claim:

1. A new and distinct variety of *Rhododendron* hybrid plant, as is herein illustrated and described.

* * * * *